United States Patent [19]

Eibl

[11] Patent Number: 4,734,225
[45] Date of Patent: Mar. 29, 1988

[54] D-MANNITE DERIVATIVES AS STARTING PRODUCTS FOR THE SYNTHESIS OF PHOSPHOLIPIDS

[75] Inventor: Hansjörg Eibl, Bovenden, Fed. Rep. of Germany

[73] Assignee: Max-Planck-Gesellschaft zur Förderung der Wissenschaften E.V., Gottingen, Fed. Rep. of Germany

[21] Appl. No.: 598,292

[22] PCT Filed: Jul. 6, 1983

[86] PCT No.: PCT/DE83/00123

§ 371 Date: Mar. 5, 1984

§ 102(e) Date: Mar. 5, 1984

[87] PCT Pub. No.: WO84/00362

PCT Pub. Date: Feb. 2, 1984

[30] Foreign Application Priority Data

Jul. 6, 1982 [DE] Fed. Rep. of Germany ....... 3225225
Oct. 27, 1982 [DE] Fed. Rep. of Germany ....... 3239858

[51] Int. Cl.[4] .................. C07C 43/00; C07F 9/00; A61K 31/00
[52] U.S. Cl. .................. 260/386; 260/403; 568/673; 568/674; 558/169; 558/177
[58] Field of Search .............. 260/386, 945, 925, 403; 568/673, 674

[56] References Cited

U.S. PATENT DOCUMENTS

| 4,159,988 | 7/1979 | Eibl et al. | 260/403 |
| 4,163,748 | 8/1979 | Eibl et al. | 260/403 |
| 4,382,035 | 5/1983 | Eibl | 260/403 |
| 4,426,525 | 1/1984 | Hozumi et al. | 260/945 |

Primary Examiner—Delbert R. Phillips
Assistant Examiner—Nathan M. Nutter
Attorney, Agent, or Firm—Felfe & Lynch

[57] ABSTRACT

The mannite derivatives have the formula (1) wherein $R'$ and $R^2$, identical or different, represent when they are identical a straight or branched alkyl, alkenyl or alkynyl group containing from 5 to 24 atoms of carbon which may be substituted by a cycloalkyl residue having from 3 to 6 atoms of carbon, an aryl, benzyloxy, allyloxy, mesyloxy residue and/or halogen atoms and when $R'$ and $R^2$ are different, they represent a straight or branched alkyl group with 1 to 24 atoms or carbon, which may be substituted by a cycloalkyl residue having from 3 to 6 atoms of carbon, an aryl, benzyloxy, allyloxy, mesyloxy residue and/or halogen atoms, with the possibility for $R'$ of being also a trityl group. From said mannite derivatives, it is possible to obtain in a simple way and with good yields the phospholipids in the form of their optical stereo isomers.

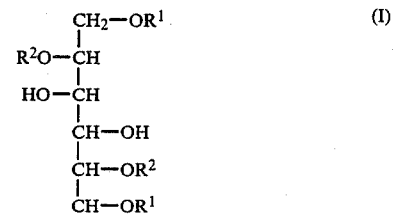

4 Claims, No Drawings

D-MANNITE DERIVATIVES AS STARTING PRODUCTS FOR THE SYNTHESIS OF PHOSPHOLIPIDS

The D-mannitol derivatives according to the invention are especially well suited as starting compounds for the synthesis of (diether) phospholipids, of (monoether) phospholipids and of (ether/ester) phospholipids and make possible the preparation of structure-, stereo- and position-isomeric compounds of these classes of substances, the biological properties of which have recently been intensively investigated.

In comparison with (diacyl) phospholipids (cf. German Patent Application P No. 31 30 867.8 of the 4th Aug., 1981), the corresponding dialkylglycerol derivatives, however, scarcely occur in animal membranes. Nevertheless, mixed alkyl/acyl-glycerol phosphatides are frequent, for example, the plasmalogens which, in organs such as heart and lungs, represent important components of the membranes. Observations are also increasing that certain ether/ester phospholipids possess, in extremely small amounts ($10^{-10}$–$10^{-11}$M), hormone-like properties, such as e.g. "PEF" (platelet activating factor), the structure of which has been described as 1-octadecyl-2-acetyl-sn-glycerol-3-phosphocholine. Therefore, there is a great interest for simple syntheses which permit a specific positioning of the alkyl radicals or acyl radicals, independently of one another, in the glycerol molecule.

Although diether phospholipids scarcely occur in animal membranes, the structures related to the ester phospholipids are of great interest in cell biology. As numerous investigations were able to show (see in this regard H. Eibl, Liposomes: From Physical Structure to Therapeutic Application, Chapter 2: Phospholipid Syntheses; ed. C. G. Knight, Elsevier, Amsterdam (1981), 19), ether phospholipids scarcely differ from ester phospholipids with regard to the physical properties but strongly in their chemical stability towards pH variations and especially in their biological stability towards the phospholipases $A_1$ and $A_2$, which can only hydrolyse ester phospholipids. Furthermore, by variation of the phosphate-trimethylammonium distance in the phosphaditylcholines, a breakdown by phospholipase C and D can, as desired, be slowed down or completely suppressed (Eibl and Kovatchev, Methods of Enzymology (1981), 72, 632). The said structure variations permit the construction of liposomes, the biological stability of which can be controlled as desired, i.e. their biological half-life time can be objectively adjusted. For the preparation of these liposomes, there are usually employed mixtures of phospholipids, such as there also occur in natural membranes (lecithins 40–80%; cephalines 20–60% and negatively charged phospholipids 5–30%). Diether phospholipids with the mentioned structure variations in the polar region are thus especially interesting for the preparation of liposomes with increased biological half-life time.

Lysolecithin derivatives possess important biological actions. Thus, lysolecithins are suitable, for example, as immunological adjuvants, which are substances which strengthen the immune response of the organism to an antigenic stimulus, thus the antibody formation (cf. published German Patent Application No. 20 09 343); (ether) lysolecithins promote the increase of the natural resistance of the organism (cf. published German Patent Application No. 20 09 342). The lysolecithin derivatives are of great importance because of their especial effectiveness on the growth of tumours; therefore, they represent an effective antitumour agent (cf. published German Patent Application No. 26 19 686).

The lysolecithin derivatives effective as anti-tumour agents possess an asymmetric carbon atom and can, therefor, occur in two stereoisomeric forms (D- and L-form), of which, however, only one form is active. Thus, for the use as medicaments, the pure stereoisomeric biologically-active forms are superior to the racemate. However, the non-biologically-active forms are, as pure stereoisomers, also valuable reagents, especially for the determination of the activity mechanism of the (ether) lecithins; as racemate administered in admixture with the biologically-active forms, on the other hand, they merely represent a burdening of the organsim, thus an undesired, inactive ballast material. The hitherto known antitumour agents are present as racemate, thus as a mixture of the D- and L-forms.

Interestingly, it was recently also found that, between normal cells and tumour cells, there exists an important difference in the enzymes present (Wykle and Snyder, The Enzymes of Biological Membranes (1976), 2, 87. In tumour cells, a 1-O-alkyl-splitting enzyme is completely missing, whereas this is always present in the microsomal fraction of normal cells.

Therefore, 1-octadecyl-2-methyl-rac-glycero-3-phosphocholine was used with some success for tumour therapy (Weltzien and Westphal, (1967), 709, 240) since normal cells, because of their 1-O-alkyl-splitting enzymes, at least partly metabolise and detoxicate these lytic and toxic substances, whereas tumour cells, because of the insufficient enzymes present, are not in a position to do this. Unfortunately, hitherto optically pure compounds could not used since the corresponding syntheses were not available.

Especially the favourable action of 1-octadecyl-2-methyl-rac-glycero-3-phosphocholine as new anti-tumour agent (cf. published German Patent Application No. 20 09 342, published German Patent Application No. 20 09 343 and published German Patent Application No. 26 19 686) was a reason to develop possibilities for the synthesis of the optically pure compounds with natural configuration (sn-glycero-3-phosphocholines) in order therewith to avoid a superfluous loading of the organism with structurally-inactive configuration and, in addition, to make possible a high dosaging of the active substance.

It is, therefore, the task of the present invention to make available routes for the synthesis of glycerol ethers but also of glycerol esters which permit a simple preparation of all desired representatives of this class of substances in optically pure form. This problem is solved by the present invention.

The subject of the invention are D-mannitol derivatives of the general formula I (beside the formula is given the stereospecific numbering, sn)

$$
\begin{array}{c|c}
sn & \\
1 & CH_2-OR^1 \\
2 & R^2O-CH \\
3 & HO-CH \\
4 & CH-OH \\
5 & CH-OR^2 \\
6 & CH_2-OR^1 \\
\end{array} \qquad (I)
$$

wherein $R^1$ and $R^2$ can be the same or different and, when $R^1$ and $R^2$ are the same, signify a straight-chained or branched alkyl, alkenyl or alkynyl group with 6 to 24 carbon atoms, which can contain cycloalkyl radicals with 3 to 6 carbon atoms, aryl radicals, benzyloxy, allyloxy, mesyloxy and/or halogen substituents, such as fluorine, bromine, iodine and especially chlorine, and when $R^1$ and $R^2$ are different, signify a straight-chained or branched alkyl group with 1 to 24 carbon atoms, which can contain cycloalkyl radicals with 3 to 6 carbon atoms, aryl radicals, benzyloxy, allyloxy, mesyloxy and/or halogen substituents, or a straight-chained or branched alkenyl or alkynyl group with 3 to 24 carbon atoms, which can contain cycloalkyl radicals with 3 to 6 carbon atoms, aryl radicals, benzyloxy, allyloxy, mesyloxy and/or halogen substituents, and $R^1$ can also be trityl and whereby preferably at least one radical $R^1$ and $R^2$ possesses more than 6 carbon atoms and especially more than 9 carbon atoms.

As substituent of $R^1$ and/or $R^2$, a cycloalkyl radical with 3 to 6 carbon atoms means, for example, cyclopropyl, cyclobutyl, methylcyclobutyl, cyclopentyl and especially cyclohexyl; an aryl radical, for example, naphthyl and especially phenyl and halogen fluorine, bromine, iodine and especially chlorine.

Preferred D-mannitol derivatives of formula I are 1,6-dibenzyl-2,5-diallyl-D-mannitol, 1,6-diallyl-2,5-dibenzyl-D-mannitol, 1,6-ditrityl-2,5-dibenzyl-D-mannitol, 1,6-ditrityl-2,5-diallyl-D-mannitol, 1,6-ditrityl-2,5-dialkyl-D-mannitol, 1,6-ditrityl-2,5-dialkenyl-D-mannitol, 1,6-ditrityl-2,5-dialkynyl-D-mannitol, 1,6-dialkyl-2,5-dibenzyl-D-mannitol, 1,6-dialkyl-2,5-diallyl-D-mannitol, 1,6-dialkyl-2,5-dialkyl-D-mannitol, 1,6-dialkenyl-2,5-dialkyl-D-mannitol, 1,6-dialkynyl-2,5-dialkyl-D-mannitol, 1,6-dialkyl-2,5-dialkenyl-D-mannitol, 1,6-dialkenyl-2,5-dialkenyl-D-mannitol, 1,6-dialkynyl-2,5-dialkenyl-D-mannitol, 1,6-dialkyl-2,5-dialkynyl-D-mannitol, 1,6-dialkenyl-2,5-dialkynyl-D-mannitol, 1,6-dialkynyl-2,5-dialkynyl-D-mannitol, especially 1,6-dioctadecyl-2,5-dimethyl-D-mannitol, 1,6-dimethyl-2,5-dioctadecyl-D-mannitol, 1,6-dioctadecyl-2,5-diallyl-D-mannitol, 1,6-dioctadecyl-2,5-dibenzyl-D-mannitol, 1,6-dioctadec-(3')-enyl-2,5-dimethyl-D-mannitol, 1,6-dioctadec-(3')-ynyl-2,5-dimethyl-D-mannitol, 1,6-dioctadecyl-2,5-ditetradecyl-D-mannitol, 1,6-dioctadecyl-2,5-didodecyl-D-mannitol, 1,6-dioctadecyl-2,5-didecyl-D-mannitol, 1,6-dioctadecyl-2,5-dioctyl-D-mannitol, 1,6-dioctadecyl-2,5-dibutyl-D-mannitol, 1,2,5,6-tetraoctadecyl-D-mannitol, 1,2,5,6-tetra-hexadecyl-D-mannitol, 1,2,5,6-tetra-(tetradecyl)-D-mannitol, 1,6-ditrityl-2,5-dioctadecyl-D-mannitol, 1,6-ditrityl-2,5-dihexadecyl-D-mannitol, 1,6-ditrityl-2,5-ditetradecyl-D-mannitol, 1,6-ditrityl-2,5-didodecyl-D-mannitol, 1,6-ditrityl-2,5-didecyl-D-mannitol, 1,6-ditrityl-2,5-dioctyl-D-mannitol and 1,6-ditrityl-2,5-dihexyl-D-mannitol.

The subject of the invention is also a process for the preparation of D-mannitol derivatives of the general formula I, which is characterised in that one tritylates 3,4-isopropylidene-D-mannitol to give 1,6-ditrityl-3,4-isopropylidene-D-mannitol, introduces into the so obtained compound the group $R^2$ by reaction with the corresponding $R^2$ mesylate, chloride, bromide or iodide or with $(R^2O)_2SO_2$, thereafter, for the case in which $R^1$ is not trityl, splits off the trityl group in weakly acidic medium, and introduces into the detritylated product the group $R^1$ by reaction with the corresponding $R^1$ mesylate, chloride, bromide or iodide or with $(R^1O)_2SO_2$ and then splits off the isopropylidene group.

Starting from the D-mannitol derivatives of formula I according to the invention, there is possible, in a simple manner, not only the preparation of the forms with natural configuration (e.g. 1-octadecyl-2-methyl-sn-glycero-phosphocholine and 1-methyl-2-octadecyl-sn-glycero-3-phosphocholine), but also the forms with non-natural configuration (e.g. 3-octadecyl-2-methyl-sn-glycero-1-phosphocholine, 3-methyl-2-octadecyl-sn-glycero-1-phosphocholine, 1-octadecyl-3-methyl-sn-glycero-2-phosphocholine and 1-methyl-3-octadecyl-sn-glycero-2-phosphocholine. Correspondingly, there were prepared phospholipids with negative and positive surface charge, which contain octadecylmethylglycerols as apolar fundamental structures. Those polar structures were especially selected which nature preferably uses for the construction of membranes. Besides the phosphocholines and phosphoethanolamines neutral in the physiological medium, there were also prepared for the first time new phosphoglycerols, phosphoserines and phosphatidic acids (ether phospholipids) which are characterised by a negative surface charge at pH 7. Corresponding structures with positive surplus charge were also prepared. The new, pure, stereoisomeric ether phospholipids are of special interest, having regard to the tumour growth-inhibiting properties, since:

1. with the optically pure representatives, a higher dosaging is possible;

2. an additional loading of the organism with structures of inactive configuration does not take place;

3. via corresponding charge patterns (positive, negative, neutral) in dialkyl phospholipids, certain tumours can possibly be selectively aimed for;

4. in logical utilisation of the observation that tumour cells do not possess 1-O-alkyl-splitting enzymes, phosphatides of the ether/ester type can be constructed according to the here-proposed methods which form double layers and thus act membrane-stabilisingly, e.g. 1-octadecyl-2-oleol-sn-glycero-3-phospho-N,N,N-(trimethyl)-hexanolamine. This phospholipid is non-toxic but a substrate for the ubiquitous phospholipases $A_2$. Therefore, not only in normal cells but also in tumour cells, by the splitting off of oleic acid, it will pass over into the toxic 1-octadecyl-sn-glycero-3-phospho-N,N,N-(trimethyl)-hexanolamine and, because of the increased phosphate-trimethylammonium distance, cannot be reacylated and detoxicated. The defence possibility via the there-present 1-O-alkyl-splitting enzymes only remains for the normal cells. The tumour cells die off by enrichment of 1-octadecyl-sn-glycero-3-phospho-N,N,N-(trimethyl)-hexanolamine.

The mannitol derivatives of the formula I can be converted quantitatively, by diol splitting and reduction, into glycerol derivatives of the following formula II. If formula II contains a benzyl radical in the sn-1-position, then, by alkylation in the 3-position and catalytic debenzylation, there can be achieved a configuration inversion to formula III. Correspondingly, formula IV arises with configuration change when the benzyl radical is anchored in the sn-2-position of the glycerol fundamental structure of formula II. Instead of benzyl, there can also be used allyl, in 1- or 3-position also trityl.

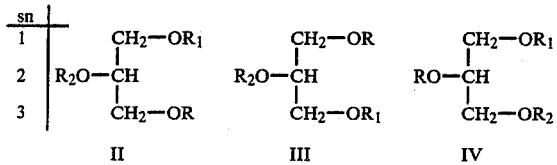

From the glycerol derivatives of the formulae II, III and IV (R=H), there can be obtained, by suitable phosphorylation steps, mostly via the non-isolated phosphoric acid dichlorides V, VI and VII, the corresponding phospholipids of the formulae VIII, IX and X (VIII, natural, sn-3-phosphate; IX non-natural, sn-1-phosphate, X, non-natural, sn-2-phosphate):

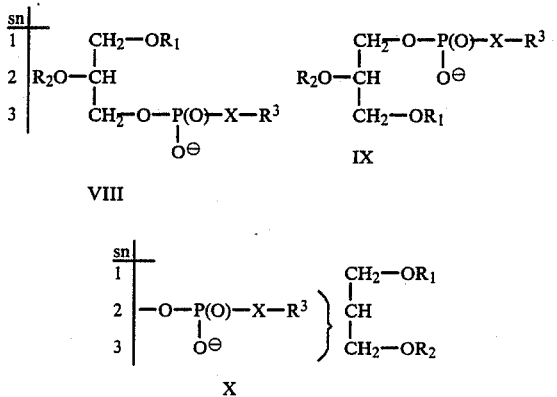

The synthesis of ester phospholipids or of ether/ester phospholipids can, starting from the correspondingly substituted glycerol derivatives of the formulae II to IV, take place according to one of the processes described in German Patent Application No. P 31 30 867.8 of the Aug. 4, 1981.

Therefore, the object of the invention are also glycerol derivatives of the general formulae II, III and IV

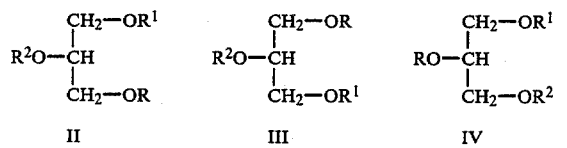

wherein $R^1$ and $R^2$ possess the meanings given above for general formula I and R represents a hydrogen atom or the radical

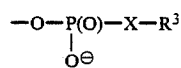

wherein X=O, NH or $NR^3$ and, when X=O, $R^3$ signifies H, alkyl, alkenyl or alkynyl with 1 to 18 carbon atoms, haloalkyl with 2 to 14 carbon atoms, 2-amino-2-carboxyethyl (serine residue), dihydroxypropyl (glycerol residue), pentahydroxyhexyl (D-mannitol residue), aminoalkyl with 2 to 14 carbon atoms, N-methylaminoalkyl with 2 to 14 carbon atoms, N,N-dimethylaminoalkyl with 2 to 14 carbon atoms, N,N,N-trimethylaminoalkyl with 2 to 14 carbon atoms, N-[(N',N',N'-trimethyl)aminoethyl]-N,N-dimethylaminoethyl, when X=NH, $R^3$ signifies alkyl or alkenyl with 1 to 10 carbon atoms, haloalkyl with 2 to 6 carbon atoms, hydroxyethyl, dihydroxypropyl, aminoalkyl, and when X=$NR^3$, $R^3$ signifies alkyl, alkenyl with 1 to 10 carbon atoms, bis-chloroethyl and whereby, when R is not a hydrogen atom, one of the radicals $R^1$ or $R^2$ in formulae II, III or IV can also be a hydrogen atom.

Further subject matter of the invention is also a process for the further working up of the D-mannitol derivatives of the formula I for the preparation of the glycerol derivatives of the formulae II, III or IV, which is characterised in that one:

(a) for the preparation of compounds of the formula II, reacts the D-mannitol derivatives of the formula I with lead tetraacetate and, in the resultant glycerol aldehyde, reduces the CHO group to the $CH_2OH$ group, (b) for the preparation of compounds of formula III, starts from D-mannitol derivatives of formula I, in which $R^1$ is a trityl group or, when $R^1$ in formula III is saturated, is also a benzyl group, reacts with lead tetraacetate, in the resultant glycerol aldehyde reduces the CHO group to the $CH_2OH$ group, in the so obtained compound introduces the group $R^1$ by reaction with the corresponding $R^1$ mesylate, chloride, bromide or iodide or with $(R^1O)_2SO_2$ and thereafter splits off the trityl group by acidic hydrolysis or the benzyl group by catalytic hydrogenolysis,.

(c) for the preparation of compounds of formula IV, starts from D-mannitol derivatives of formula I, in which $R^1$ is an alkyl group and $R^2$ an allyl group or, when $R^1$ and $R^2$ in formula IV are saturated, is also a benzyl group, reacts with lead tetraacetate, in the resultant glycerol aldehyde derivative reduces the CHO group to the $CH_2OH$ group, in the so obtained compound possibly rearranges the allyl group into a propenyl group, introduces $R^2$ by reaction with the corresponding $R^2$ mesylate, chloride, bromide or iodide or with $(R^2O)_2SO_2$ and thereafter again splits off the propenyl group by acidic hydrolysis or the benzyl group by catalytic hydrogenolysis and, if desired, into the compounds obtained according to (a), (b) or (c), in which R signifies a hydrogen atom, introduces the radical

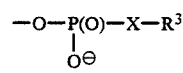

in per se known manner and, when desired, in a compound of formula II, III or IV, in which R does not signify a hydrogen atom, converts a benzyl or allyl radical $R^1$ or $R^2$ in per se known manner into a hydrogen atom.

If desired or expedient, the processes can also be so carried out that one starts from a product obtained according to one of the process steps and carries out the remaining process steps.

The tritylation (introduction of the trityl group) preferably takes place by reaction with trityl chloride in the presence of a tertiary amine, e.g. triethylamine, in a suitable organic solvent. Solvents suitable for this reaction are e.g. polar organic solvents, such as for example secondary or tertiary alkanols, for example tert.-butanol, dioxan, tetra-hydrofuran, but also benzene. The reaction is normally carried out at the boiling temperature of the solvent. The ending of the reaction can be ascertained by thin layer chromatography. Before the further working up (e.g. introduction of the radical $R^2$), it is expedient to subject the product obtained to a purification step. For this purpose, for example, the main amount of the solvent, for example tert.-butanol, is evaporated off in a vacuum, the residue taken up in diisopropyl ether, the ether phase washed twice with water and then evaporated.

The reaction with alkyl mesylate, chloride, bromide or iodide or with dialkyl sulphate can take place under the known conditions usual for such a reaction. As solvents, there can be used the solvents usual for such reactions, such as for example tertiary alcohols, tetrahydrofuran, xylene or dioxan. The reaction temperatures normally lie above room temperature, preferably between 50° and 100° C., for example at the boiling temperature of the solvent. As bases, there are used alkylates, especially potassium tert.-butylate. For the introduction of long-chained alkyl radicals, it is expedient, instead of the halides, to use the corresponding mesylates. The ending of the reaction can be ascertained by thin layer chromatography. Before the further working up, it is expedient to subject the product obtained to a purification step. For this purpose, the reaction mixture is mixed, for example, with diisopropyl ether and extracted with water. The ether phase is evaporated and can be purified chromatographically, for example on silica gel.

The splitting off of the trityl group takes place under weakly acidic conditions, preferably at a pH value of 4 to 6, whereby the most favourable value can easily be ascertained having regard to the other substituents in the molecule. The allyl and benzyl protective groups are hereby completely stable. The reaction can be carried out in an aqueous or aqueous-organic but also in a purely organic medium, such as for example in absolute ethanol, in the presence of HCl or $H_2SO_4$. The organic solvent can thereby be one miscible with water but also one only partly miscible with water or scarcely miscible with water. The reaction takes place, especially in the case of working in a two-phase system, advantageously with vigorous stirring. The temperature amounts, in general, to 20° to 80° C. For the improvement of the solubility, it can be expedient to add thereto a higher alcohol, such as for example propanol-(2), in small amounts. For example, the tritylated compound is dissolved in acetone, then the equal amount of concentrated sulphuric acid-containing methanol (methanol/sulphuric acid=1/100) is added thereto and heated at 50° C. for about 60 minutes. For purification, the reaction mixture obtained is mixed, for example, with diisopropyl ether, washed twice with water and thereafter with aqueous 1M sodium bicarbonate. The ether phase is evaporated and can be purified chromatographically, for example on silica gel.

The splitting off of the isopropylidene group can take place under acidic conditions in an organic-aqueous medium. Thus, for example, the reaction product obtained after the splitting off of the trityl group and introduction of the radical $R^1$ is mixed, in a mixture of propanol-(2)/methanol (1/1), with 2N sulphuric acid (50 ml. to 1 l. of solvent) and boiled under reflux. The end of the reaction can be ascertained by TLC verification.

The splitting of the mannitol fundamental structure into two glycerol molecules takes place by reaction with lead tetraacetate in an organic solvent which is inert towards lead tetraacetate, such as for example benzene, toluene, tetrahydrofuran or dioxan. For example, the lead tetraacetate is added portion-wise to the solution at room temperature and with stirring; after ending of the reaction (disappearance of the starting product, TLC verification), the reaction solution is then washed twice with water and the solvent (for example benzene) evaporated off.

The reduction of the CHO group to the $CH_2OH$ group can take place in per se known manner by reduction with a metal hydride in a suitable organic solvent, for example with alkali metal aluminium hydride, such as for example lithium aluminium hydride, or with alkali metal borohydride, such as for example potassium borohydride, and especially with sodium borohydride. The reduction preferably takes place with sodium borohydride in methanol as solvent.

The introduction of the benzyl group can take place in per se known manner, such as for example by reaction with benzyl chloride under the conditions given above for the reaction with alkyl halides.

The splitting off of the benzyl group takes place by catalytic hydrogenolysis. The reaction conditions correspond to the usual conditions. In particular, one carries out the hydrogenolysis in an inert solvent, such as for example ethanol, in the presence of a palladium or platinum/palladium catalyst, preferably at room temperature and under normal pressure (cf. H. Eibl et al., Liebigs Annalen Chemie, 738 (1970), 161).

The splitting off of the allyl group (rearrangement into propenyl and subsequent splitting off of propenyl) can take place according to two different methods, namely (1) under alkaline conditions, such as for example with potassium tert.-butylate in dimethylformamide and subsequent splitting with bromine in buffered solution at a pH value of about 5 to 6, or (2) by rearrangement in the presence of a palladium-(charcoal) catalyst with the formation of the propenyl group, which is unstable under these conditions and splits off spontaneously, whereby it is expedient to work in 80% methanol which contains 20% formic acid, at reflux temperature. In general, variant 1, i.e. the splitting off with bromine, is preferred. For the splitting off of the propenyl group in the 1-position, iodine can also be used (Eibl and Lands, Biochemistry, 9 (1970), 423). Whereas, however, a splitting off of the propenyl group in the 2-position is not possible at all with iodine, such a splitting off can, surprisingly, be carried out completely with bromine and in a few minutes.

The introduction of the radical

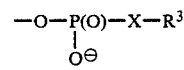

takes place in per se known manner, such as for example by reaction with halo-(preferably bromo-)alkyl phosphoric acid dichloride (cf. Hirth and Berchthold, Pharm. Acta Helv., 33 (1958), 349) or preferably by reaction with $POCl_3$ in the presence of a tertiary amine, especially of triethylamine, and subsequent reaction of the glycerol phosphoric acid dichloride obtained with the corresponding halo-(preferably bromo-)-alkanol (H. Eibl, Proc. Nat. Acad. Sci. USA, 75 (1978), 4074; H. Eibl and A. Nicksch, Chem. Phys. Lipids, 22 (1978) 1;

W. Diembeck and H. Eibl, Chem. Phys. Lipids, 24 (1979), 237) and quite preferably by reaction with POCl$_3$ in the presence of a tertiary amine, subsequent reaction with the corresponding bromoalkanol in the presence of a tertiary amine and subsequent methanolysis, after which then follows, for example, the reaction with the corresponding amine. However, the glycerol phosphoric acid dichloride can also be reacted with the corresponding aminoalcohol and the amino group e.g. subsequently alkylated.

The reaction with the amine takes place in per se known manner (cf. H. Eibl and A. Nicksch, Chem. Phys. Lipids, 22 (1978), 1; W. Diembeck and H. Eibl, Chem. Phys. Lipids, 24 (1979), 237), as well as the subsequent alkylation of the free amino group. As solvent for the reactions with phosphorus oxychloride and haloalkanol, there can serve, for example, dioxan, chloroform, carbon tetrachloride, methylene chloride and especially tetrahydrofuran. Expediently, the product (0.1 mol) obtained after the process step of the reduction with sodium borohydride is, for example, dissolved in 500 ml. tetrahydrofuran and mixed with 0.2 mol triethylamine. This solution is added dropwise at 20° C. to phosphorus oxychloride (0.15 mol) in 100 ml. tetrahydrofuran. After ending of the reaction (TLC verification), it is filtered off from precipitated triethylamine hydrochloride, mixed with toluene and evaporated for the removal of excess POCl$_3$. One takes up the residue in 400 ml. tetrahydrofuran and mixes with 0.2 mol triethylamine. At 20° to 30° C., 0.2 mol bromoethanol in 200 ml. tetrahydrofuran are added dropwise. After ending of the reaction (TLC verification), it is filtered off from triethylamine hydrochloride and, for the hydrolysis of the PCl compounds, mixed with 80 ml. of water. After ending of the reaction (TLC verification), it is mixed with 600 ml. chloroform and shaken with 600 ml. of water. The chloroform phase contains the reaction product, which is then reacted with trimethylamine, preferably in chloroform/propanol-(2) (1/1) as solvent. For this purpose, for example, to the solution of the reaction product in chloforom obtained in the preceding step, there is added a 30% solution of trimethylamine in propanol-(2) until a ratio of chloroform/propanol-(2) of 1/1 is obtained.

According to the process according to the invention starting from the D-mannitol derivatives of general formula I, it is possible to obtain phospholipids in a simple manner and with good yields in the form of their optically pure D- or L-stereoisomers. The known phospholipid syntheses start from 1,2-isopropylidene-sn-glycerol, the synthesis of which is bound up with difficulties (cf. for example H. Eibl, Chem. Phys. Lipids, 1981, 28, 1–5). Thus, the yields of 1,2-isopropylidene-sn-glycerol from D-mannitol amount to only about 40% and, furthermore, without laborious countermeasures in the case of the standing of this intermediate compound in the air, racemisation can take place by the action of carbon dioxide, whereby a stereo-specific synthesis is not possible without previous work-intensive racemate splitting. With the process according to the invention, these difficulties can be overcome. Thus, for example, the starting product for the preparation of the D-mannitol derivatives of formula I (3,4-isopropylidene-D-mannitol) can be obtained from D-mannitol in over 90% yield (L. F. Wiggins, J. Chem. Soc., 13 (1946).

The D-mannitol derivatives of formula I are, consequently, valuable intermediate products for the stereo-specific synthesis of glycerol derivatives, especially of phospholipids of general formulae II to IV.

By position-specific syntheses, there can thereby be positioned, as desired, with complete maintenance of configuration, the radicals R$^1$, R$^2$ and the phosphorus-containing radical, whereby the specific positioning already takes place in the mannitol fundamental structure. This is shown, for example, in the following reaction schemes A to F for some preferred compounds. Surprisingly, it is thereby possible to obtain from the intermediate products of the formula I, in spite of subsequent reaction with lead tetraacetate and reduction, the pure stereoisomeric forms in good yields.

In comparison with earlier investigations with racemic compounds, such as e.g. 1-octadecyl-2-methyl-glycero-3-phosphocholine, there are described, for the first time, the optically pure enantiomers. As already mentioned, the synthesis of ether phospholipids with negative or positive excess charge, furthermore opens up new possibilities for the selective enrichment of tumour growth-inhibiting substances in tissues. The new substances with negative or positive excess charging are very similar to the human-occurring phospholipids, in contra-distinction to the previously used racemates. This applies especially for the compounds of plasmalogen-like structure (reactions schemes D and E).

The subject of the invention are also medicaments which contain, as active material, one or more of the compounds of formulae II to IV according to the invention and especially II in which R signifies the radical

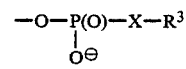

Besides the usual pharmaceutical confectioning and/or dilution agents, these medicaments can also contain, besides the compounds of the formulae II to IV, possibly also still further active materials for the enhancement of the therapy insofar as these do not show undesired side effects together with the compounds of formula II to IV according to the invention.

The effectiveness of the compounds of general formula I on the growth of tumours is expediently demonstrated on tumours in experimental animals. For this purpose, various experimental tumours are used, for example, the Ehrlich ascites tumour, a methylcholanthrene-induced tumour and a myeloma tumour in mice, furthermore a chemically-induced tumour. The antitumour substances are administered parenterally into the tumour-bearing experimental animals. The intravenous and the intra- or subcutaneous administration is preferred. Oral administration is also not excluded in the case of correspondingly high dosage of the antitumour agent and in the case of a physiologically compatible composition, e.g. in capsules.

As dosaging, there has proved to be expedient, in the case of the parenteral administration, to use about 0.05 to 5 mg./kg. body weight. In order to allow the antitumour agents to persist in the circulation for a comparatively long time, it is frequently a good idea to administer the agents daily or in 2- or 3-day intervals.

In the reaction schemes A to F, there are summarised the processes for the synthesis of the compounds according to the invention. In reaction schemes A to C, it is shown how, from the D-mannitol derivatives of the formula I, there can be obtained the three stereoisomeric glycerol derivatives of the formulae II to IV.

From each stereoisomeric form, there can be obtained, for a dialkyl ether pair, two position-isomeric forms; in this way, all six possible isomeric forms can be obtained from one intermediate product by simple synthesis steps. In the reaction schemes D and E, there are found statements how unsaturated radicals can be positioned by way of the example of the positioning of unsaturated radicals in sn-1-position and sn-2-position of the glycerol molecule. Correspondingly, according to schemes A to C, unsaturated radicals can also be introduced into 2n-3-position. In reaction scheme F, there are then finally described the possibilities for the introduction of the phosphate radical. In the reaction schemes, Ip signifies the isopropylidene radical.

(A) 1-Octadecyl-2-methyl-sn-glycerol and 1-methyl-2-octadecyl-sn-glycerol (by exchange methylation against octadecylation and vice versa)

Configuration: natural (sn-3-OH)

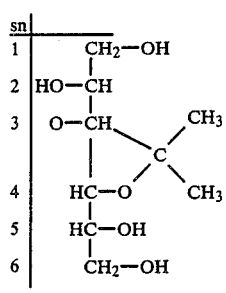

I': (a) tritylation ⟶ 1,6-ditrityl-3,4-Ip-D-mannitol
(b) alkylation ⟶ 1,6-ditrityl-2,5-dimethyl-3,4-Ip-D-mannitol
(c) detritylation ⟶ 2,5-dimethyl-3,4-Ip-D-mannitol
(d) alkylation ⟶ 1,6-dioctadecyl-2,5-dimethyl-3,4-Ip-D-mannitol
(e) deacetonisation ⟶ I; 1,6-dioctadecyl-2,5-dimethyl-D-mannitol

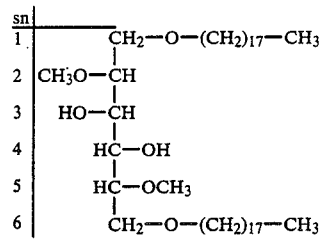

I: (f) diol splitting ⟶ octadecyl-2-methyl-sn-glycerol-3-aldehyde
(g) reduction ⟶ II; 1-octadecyl-2-methyl-sn-glycerol

(B) 3-Octadecyl-2-methyl-sn-glycerol (see Scheme, via configuration reversal by specific alkylation of 1-benzyl-2-methyl-sn-glycerol) and 3-methyl-2-octadecyl-sn-glycerol (by exchange methylation against octadecylation and vice versa).

Configuration: non-natural (sn-1-OH)

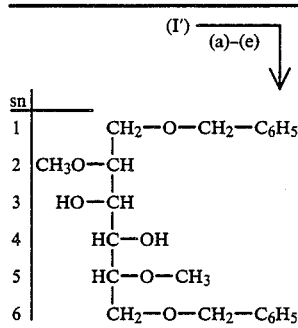

I' (a) tritylation ⟶ 1,6-ditrityl-3,4-Ip-D-mannitol
(b) alkylation ⟶ 1,6-ditrityl-2,5-dimethyl-3,5-Ip-D-mannitol
(c) detritylation ⟶ 2,5-dimethyl-3,4-Ip-D-mannitol
(d) alkylation ⟶ 1,6-dibenzyl-2,5-dimethyl-3,4-Ip-D-mannitol
(e) deacetonisation ⟶ I; 1,6-dibenzyl-2,5-dimethyl-D-mannitol

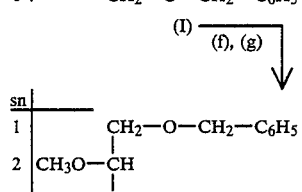

I: (f) diol splitting of IV ⟶ 1-benzyl-2-methyl-sn-glycerol-3-aldehyde
(g) reduction ⟶ II; 1-benzyl-2-methyl-sn-glycerol

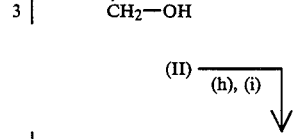

Configuration reversal:
II: (h) alkylation ⟶ 1-benzyl-2-methyl-3-octadecyl-sn-glycerol
(i) cat. debenzylation ⟶ III; 3-octadecyl-2-methyl-sn-glycerol

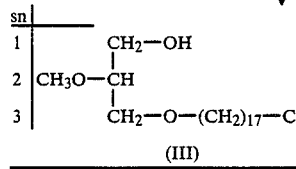

(C) 1-Methyl-3-octadecyl-sn-glycerol (via configuration change by specific alkylation of 1-methyl-2-benzyl-sn-glycerol) and 1-octadecyl-2-methyl-sn-glycerol (by exchange methylation against octadecylation and vice versa).
Configuration: non-natural (sn-2-OH)
(D) Introduction of alkenyl radicals into the (sn-2-)-position of the glycerol (natural configuration)
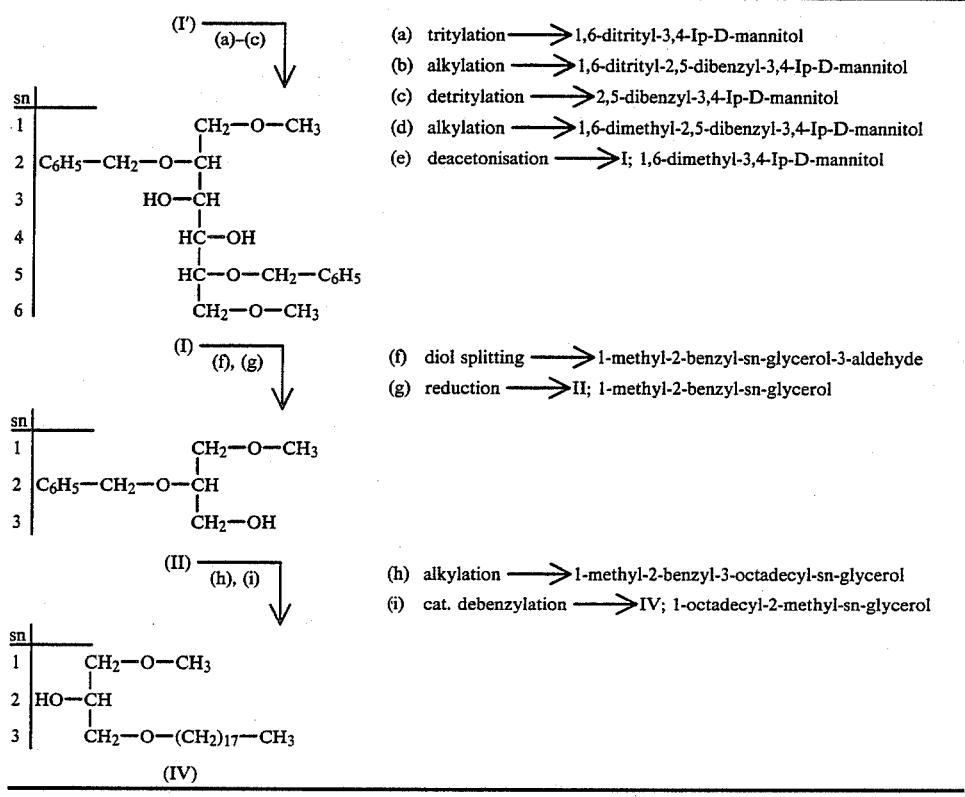
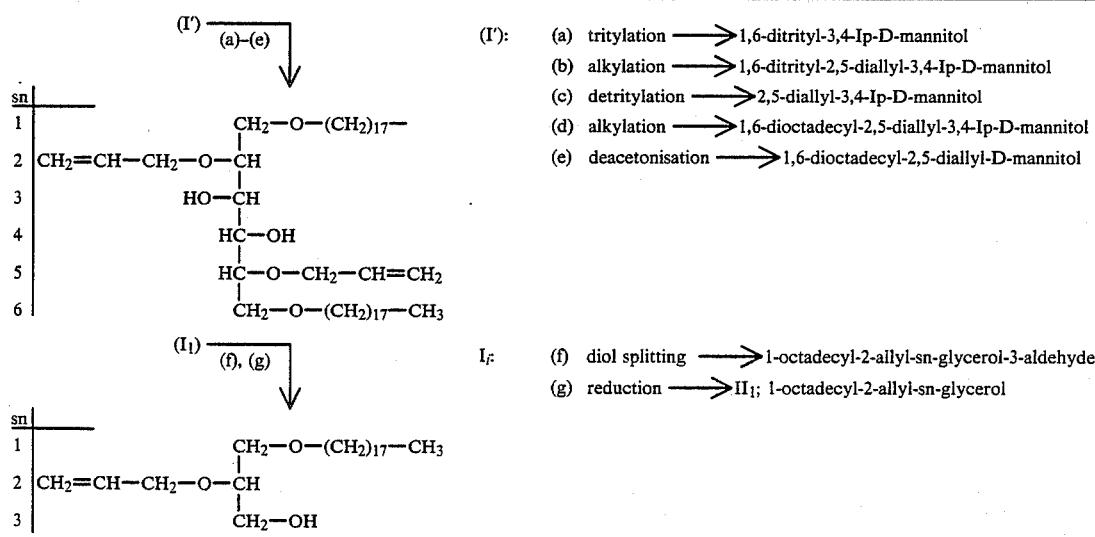

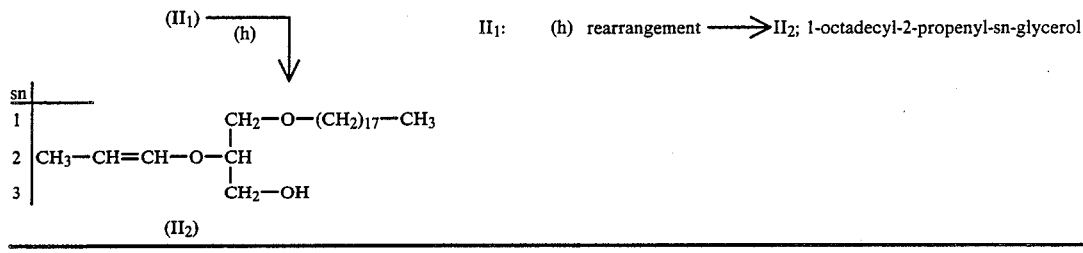

II₁: (h) rearrangement ⟶ II₂; 1-octadecyl-2-propenyl-sn-glycerol (E) Introduction of alkenyl radicals into the sn-1-position of the glycerol (natural configuration)

(F) Phospholipids from diether glycerols

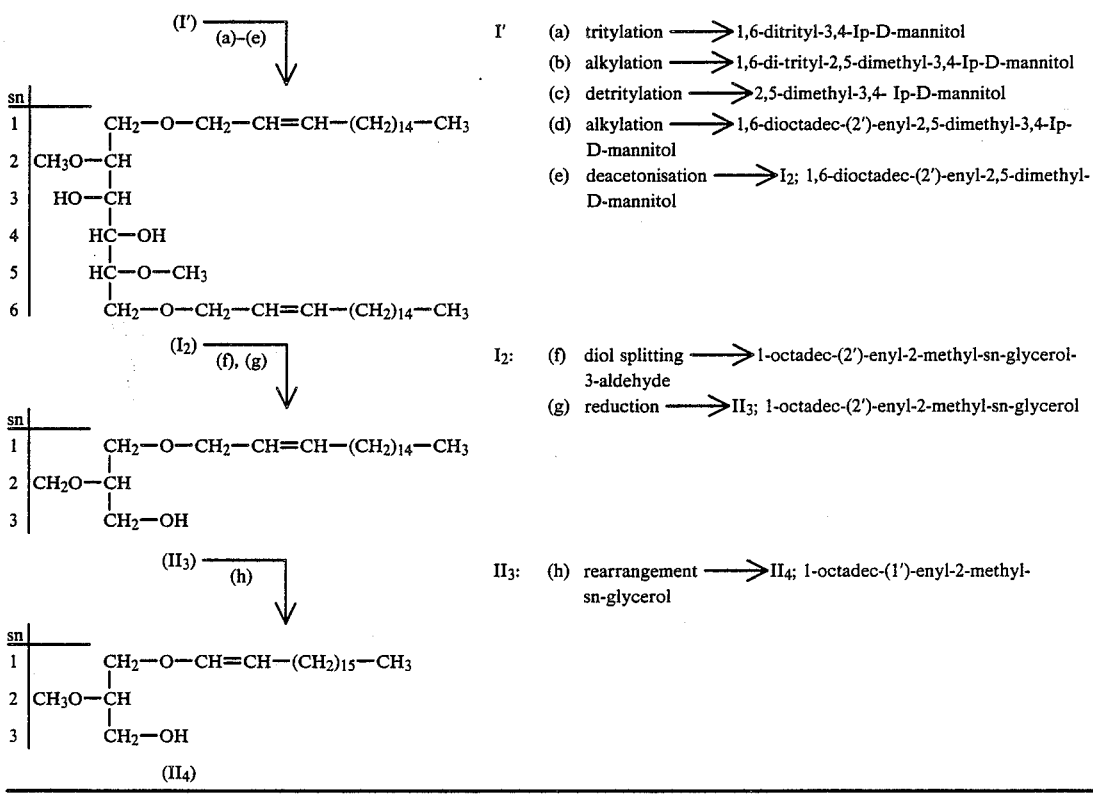

I': (a) tritylation ⟶ 1,6-ditrityl-3,4-Ip-D-mannitol
(b) alkylation ⟶ 1,6-di-trityl-2,5-dimethyl-3,4-Ip-D-mannitol
(c) detritylation ⟶ 2,5-dimethyl-3,4- Ip-D-mannitol
(d) alkylation ⟶ 1,6-dioctadec-(2')-enyl-2,5-dimethyl-3,4-Ip-D-mannitol
(e) deacetonisation ⟶ I₂; 1,6-dioctadec-(2')-enyl-2,5-dimethyl-D-mannitol I₂: (f) diol splitting ⟶ 1-octadec-(2')-enyl-2-methyl-sn-glycerol-3-aldehyde
(g) reduction ⟶ II₃; 1-octadec-(2')-enyl-2-methyl-sn-glycerol II₃: (h) rearrangement ⟶ II₄; 1-octadec-(1')-enyl-2-methyl-sn-glycerol R'OH (R' = radical of II to IV)
↓ phosphorylation

| | | |
|---|---|---|
| R'O—POCl$_2$(V-VII) | | |
| (1)→ R'O—PO—ONa(V-VII): <br> \|<br>OH | (1) hydrolysis ⟶ phosphatidic acid (VIII$_1$-X$_1$) | |
| (2)→ R'O—PO—ONa <br> \|<br>OCH$_2$—CH$_2$<br>\|<br>OH | (2) glycol; hydrolysis ⟶ phosphatidyl glycols (VIII$_2$-X$_2$) | |
| (3)→ R'O—PO—O$^\ominus$ <br> \|<br>O—CH$_2$—CH$_2$—$\overset{\oplus}{N}$H$_3$ | (3) ethanolamine; acidic hydrolysis ⟶ phosphatidyl ethanolamines (VIII$_3$-X$_3$) | |
| (4)→ R'O—PO—ONa <br> \|<br>O—(CH$_2$)$_x$H | (4) alkanols (x = 1-18) hydrolysis ⟶ phosphatidic acid alkyl esters (VIII$_4$-X$_4$) | |
| (5)→ R'—PO—O$^\ominus$ <br> \|<br>O—(CH$_2$)$_y$—$\overset{\oplus}{N}$(CH$_3$)$_3$ | (5) bromoalkanols (y = 2-12); hydrolysis; amination ⟶ phosphatidylcholines (VIII$_5$-X$_5$) | |
| (6)→ —$\overset{\oplus}{N}$(CH$_3$)$_2$H | (6) N,N—dimethyl-phosphatidyl ethanolamines (VIII$_6$-X$_6$) | |
| (7)→ —$\overset{\oplus}{N}$CH$_3$H$_2$ | (7) N—methyl-phosphatidylethanolamine (VIII$_7$-X$_7$) | |
| (8)→ —$\overset{\oplus}{N}$H$_3$ | (8) phosphatidylethanolamines (VIII$_8$-X$_8$) | |
| (9)→ R'O—PO—ONa <br> \|<br>O—CH$_2$—CH—CH$_2$<br>\| \|<br>OH CH$_2$—OH | (9) 1,2-isopropylidene-glycerol; basic and acidic hydrolysis ⟶ phosphatidyl glycerol (VIII$_9$-X$_9$) | |
| R'O—POCl$_2$ (V-VII) | | |
| (10)→ R'O—PO—ONa <br>(XX) \|<br>O—CH$_2$—CH—$\overset{\oplus}{N}$H$_3$<br>\|<br>COO$^\ominus$ | (10) hydrolysis; N—carbobenzoxy-serine benzyl ester; cat. hydrogenolysis ⟶ phosphatidyl-serine (V$_7$-VII$_7$) | |
| (11)→ R'O—PO—ONa <br>(XXI) \| CH$_2$—CH$_2$—Cl<br>\| /<br>N<br>\\<br>CH$_2$—CH$_2$—Cl | (11) amines; hydrolysis ⟶ phosphatidic acid amide (V$_8$-VII$_8$) | |

EXAMPLES

Stereo- and position-specific synthesis of diether glycerols (saturated hydrocarbon radicals, reaction schemes A to C)

Tritylation A–C, a:

Starting product is the 3,4-isopropylidene-D-mannitol (I') readily obtainable according to L. F. Wiggins (J. Chem. Soc., 13 (1946). A solution of I' (0.1 mol) in 500 ml. tert.-butanol is mixed with trityl chloride (0.2 mol) and triethylamine (0.3 mol). One boils under reflux until completion of the reaction (TLC verification). The main amount of the tert.-butanol is stripped off in a vacuum, the residue is taken up in 500 ml. diisopropylidene ether and extracted with water. The diisopropyl ether phase is evaporated and the oily residue, preponderantly 1,6-ditrityl-3,4-isopropylidene-D-mannitol (0.1 mol), taken up in 1 l. dioxan (solution A–C, a).

Alkylation A–C, b:

The solution A–C, a (0.1 mol) is mixed with potassium tert.-butylate (0.2 mol) and boiled under reflux. With stirring, methyl iodide or dimethyl sulphate (0.3 mol) is added dropwise (A and B, b) or mixed with benzyl chloride (C, b). One boils until completion of the reaction (TLC verification) and mixes with 1 l. diisopropyl ether. After extraction of the diisopropyl ether phase with water, this is evaporated and the residue purified on silica gel by chromatography. One obtains in the reactions A, B-b 1,6-ditrityl-2,5-dimethyl-3,4-isopropylidene-D-mannitol and in C, b 1,6-ditrityl-2,4-dibenzyl-3,4-isopropylidene-D-mannitol in a yield of 85–90%.

Detritylation A–C, c:

The acid-labile trityl group is removed in the presence of sulphuric acid in acetone. For this purpose, the particular ditrityl compound (A–C, b; 0.1 mol) is dissolved in 500 ml. acetone, mixed with 500 ml. methanol which contains 5 ml. concentrated sulphuric acid and heated to 50° C. on a water-bath. After 60 minutes, the trityl radicals are split off from the 1,6-position. One mixes with 1 l. diisopropylidene ether and extracts twice with 1 l. amounts of water, finally with 1 l. aqueous 1M $NaHCO_3$. The diisopropyl ether phase is evaporated and purified on silica gel. One obtains A, B–c 2,5-dimethyl-3,4-isopropylidene-D-mannitol and C, c 2,5-dibenzyl-3,4-isopropylidene-D-mannitol in yields of 90–95%.

Alkylation A–C, d:

For the introduction of the alkyl or benzyl radicals into the 1,6-position, the intermediate products A–C, c, in each case 0.1 mol, are dissolved in 500 ml. toluene and mixed with potassium tert.-butylate (0.2 mol). One boils under reflux and adds dropwise, while stirring, in each case 0.2 ml of the corresponding compounds; for example, for the preparation of A, d octadecyl mesylate bromide or iodide, for the preparation of B, d benzyl chloride or bromide and for the preparation of C, d methyl iodide or dimethyl sulphate. After conclusion of the reaction (TLC verification), the toluene phase is extracted twice with water and evaporated. The residue from reaction A, d is mainly 1,6-dioctadecyl-2,5-dimethyl-3,4-isopropylidene-D-mannitol, from B, d 1,6-dibenzyl-2,5-dimethyl-3,4-isopropylidene-D-mannitol or from C, d 1,6-dimethyl-2,5-dibenzyl-3,4-isopropylidene-D-mannitol; yields about 90%.

Deacetonisation A–C, e:

For the removal of the isopropylidene group in the 3,4-position of the mannitol derivatives, one uses aqueous sulphuric acid in 2-propanol/methanol 1:1. The particular intermediate product (0.1 mol) from A–C, d in 1 l. of the solvent mixture, is mixed with 50 ml. 2N $H_2SO_4$ and boiled under reflux up to the complete splitting off of the isopropylidene group (TLC verification). One mixes with 1 l. diisopropyl ether, extracts twice with 1 l. amounts of water and evaporates the diisopropylidene ether phase. The intermediate products $A_I$, $B_I$ and $C_I$ are purified by chromatography on silica gel and characterised by microanalysis; yield 90–95%.

The following compounds of formula I were prepared in this way:

1,6-dioctadecyl-2,5-dimethyl-D-mannitol ($C_{44}H_{90}O_6$; 715.20). Calc.: C 73.89, H 12.69. Found: C 74.01, H 12.84.

1,6-ditetradecyl-2,5-dimethyl-D-mannitol
($C_{36}H_{74}O_6$; 602.99).
calc.: C 71.71, H 12.37. found: C 71.76, H 12.42.

1,6-didocosanyl-2,5-dimethyl-D-mannitol ($C_{52}H_{106}O_6$; 827.42).
calc.: C 75.48, H 12.91. found: C 75.69, H 12.94.

1,6-dioctadecyl-2,5-dipentyl-D-mannitol ($C_{52}H_{106}O_6$; 827.42).
calc.: C 75.48, H 12.91. found: C 75.84, H 13.01.

1,6-dioctadecyl-2,5-didodecyl-D-mannitol ($C_{66}H_{134}O_6$; 1023.798).
calc.: C 77.43, H 13.19. found: C 77.41, H 13.27.

1,6-dibenzyl-2,5-dimethyl-D-mannitol ($C_{22}H_{30}O_6$; 390.48).
calc.: C 67.67, H 7.74. found: C 67.66, H 7.76.

1,6-dimethyl-2,5-dibenzyl-D-mannitol ($C_{22}H_{30}O_6$; 390.48).
calc.: C 67.67, H 7.74. found: C 67.82, H 7.91.

Diol splitting A–C, f:

The intermediate products of the formula I (in each case 0.1 mol) are dissolved in 500 ml. benzene and mixed portionwise with lead tetraacetate (about 0.1 mol) until the starting product is no longer to be detected (TLC verification). The reaction mixture is washed twice with 500 ml. amounts of water, the benzene phase is evaporated and the residue is taken up in 500 ml. methanol.

Reduction A–C, g:

The solution of the aldehydes in methanol is mixed portionwise with $NaBH_4$ (about 0.1 mol) until the aldehyde detection is negative. One mixes with 500 ml. diisopropyl ether and shakes out twice with water. The diethyl ether phase is evaporated and the residue chromatographed on silica gel. One obtains the compounds of the formula II in yields of 90.

The following compounds of formula II were prepared in this way:

1-octadecyl-2-methyl-sn-glycerol ($C_{22}H_{46}O_3$; 358.61).
calc.: C 73.69, H 12.93. found: C 73.71, H 12.96.

1-tetradecyl-2-methyl-sn-glycerol ($C_{18}H_{38}O_3$; 302.502).
calc.: C 71.47, H 12.66. found: C 71.55, H 12.70.

1-docosanyl-2-methyl-sn-glycerol ($C_{26}H_{54}O_3$; 414.72).
calc.: C 75.30, H 13.13. found: C 75.35, H 13.13.

1-octadecyl-2-pentyl-sn-glycerol ($C_{26}H_{54}O_3$; 414.72).
calc.: C 75.30, H, 13.13. found: C 75.37, H 13.17.

1-octadecyl-2-dodecyl-sn-glycerol ($C_{33}H_{68}O_3$; 512.91).
calc.: C 77.28, H 13.36. found: C 77.35, H 13.31.

1-benzyl-2-methyl-sn-glycerol ($C_{11}H_{16}O_3$; 196.25).
calc.: C 67.32, H 8.22. found: C 67.46, H 8.27.

1-methyl-2-benzyl-sn-glycerol ($C_{11}H_{16}O_3$; 196.25).
calc.: C 67.32, H 8.22. found: C 67.39, H 8.23.

Alkylation B or C, h:

The compound A II is directly available for the phosphorylation. In compounds B II and C II, before the phosphorylation, octadecyl radicals are introduced and the desired position in the glycerol molecule is freed. For this purpose, the intermediate products B II and C II (in each case 0.1 mol) are dissolved in 500 ml. toluene and mixed with potassium tert.-butylate (0.1 mol). One boils under reflux and adds dropwise, with stirring, a solution of octadecyl mesylate (in each case 0.1 mol) in 100 ml. toluene and obtains from reaction B, h 1-benzyl-2-methyl-3-octadecyl-sn-glycerol and from reaction C, h 1-methyl-2-benzyl-3-octadecyl-sn-glycerol. After ending of the reaction (TLC verification), the toluene phase is extracted twice with water, evaporated and the residue purified by chromatography on silica gel. The yields lie at 95%.

Catalytic debenzylation B or C, i:

The products from the reaction B or C, h (0.1 mol) are dissolved in 200 ml. diisopropyl ether, mixed with 4 g. Pd/C (10%) and 0.4 g. palladium black and left, while stirring, in an $H_2$ atmosphere so long that the $H_2$ take-up is concluded. The compounds B III and C IV result quantitatively and, after removal of the diisopropyl ether, can be used directly for the phosphorylation.

The following compounds were prepared in this way:

Compounds of formula III:

3-octadecyl-2-methyl-sn-glycerol ($C_{22}H_{46}O_3$; 358.61).
calc.: C 73.69, H 12.93. found: C 73.82, H 12.95.

3-octadecyl-2-pentyl-sn-glycerol ($C_{26}H_{54}O_3$; 414.72).
calc.: C 75.30, H 13.13. found: C 75.45, H 13.19.

3-octadecyl-2-dodecyl-sn-glycerol ($C_{33}H_{68}O_3$; 512.91).
calc.: C 77.28, H 13.36. found: C 77.35, H 13.41.

Compounds of formula IV:

3-octadecyl-1-methyl-sn-glycerol ($C_{22}H_{46}O_3$; 358.61).
calc.: C 73.69, H 12.93. found: C 73.79, H 12.98.

3-octadecyl-1-pentyl-sn-glycerol ($C_{26}H_{54}O_3$; 414.72).
calc.: C 75.30, H 13.13. found: C 75.25, H 13.11.

3-octadecyl-1-dodecyl-sn-glycerol ($C_{33}H_{68}O_3$; 512.91).
calc.: C 77.28, H 13.36. found: C 77.27, H 13.45.

Introduction of alkenyl radicals into the sn-2- or sn-1-position of glycerol (reaction schemes D and E)

The individual reaction steps are illustrated in reaction schemes D and E and systematically divided into the introduction of alkenyl radicals in the sn-2-position of glycerol and the introduction of alkenyl radicals into the sn-1-position of glycerol. For the introduction of alkynyl radicals, the same precautions must be observed as for the alkenyl radicals. The most important limitation consists in the fact that benzyl radicals cannot be used as protective groups. For the positioning of the radicals in 1- and 2-position, however, the trityl protective group is sufficient and this leads to the interesting representatives with natural configuration, i.e. free hydroxyl group in the sn-3-position. A configuration reversal according to reaction scheme B h, 1 is also easily possible by replacement of the benzyl group by trityl. However, in reaction scheme C h, i, benzyl cannot be replaced by trityl. One can here use the allyl protective group.

The individual reaction steps are, here too, again explained on the basis of special examples. There is described the synthesis of 1-octadecyl-2-allyl-sn-glycerol and of 1-octadecyl-2-propenyl-sn-glycerol (reaction scheme D), as well as of 1-octadec-(2')-enyl-2-methyl-sn-glycerol and of 1-octadec-(1')-enyl-2-methyl-sn-glycerol (reaction scheme E).

Tritylation D or E, a:

Starting prouct is the 3,4-isopropylidene-D-mannitol (I') readily obtainable according to L. F. Wiggins (J. Chem. Soc., 13 (1946). A solution of I' (0.1 mol) in 500 ml. tert.-butanol is mixed with trityl chloride (0.2 mol) and triethylamine (0.3 mol). One boils under reflux up to completion of the reaction (TLC verification). The main amount of the tert.-butanol is stripped off in a vacuum, the residue taken up in 500 ml. diisopropylidene ether and extracted with water. The diisopropyl ether phase is evaporated and the oily residue, preponderantly 1,6-ditrityl-3,4-isopropylidene-D-mannitol (0.1 mol), is taken up in 1 l. dioxan (solution D or E, a).

Alkylation D or E, b:

The solution D or E, a (0.1 mol) is mixed with potassium tert.-butylate (0.2 mol) and boiled under reflux. While stirring, allyl chloride (0.3 mol) is dropped in (D, b) or mixed with methyl iodide (E, b). One boils until completion of the reaction (TLC verification) and mixes with 1l. diisopropyl ether. After extraction of the diisopropyl ether phase with water, this is evaporated and the residue purified on silica gel by chromatography. One obtains according to D, b 1,6-ditrityl-2,5-diallyl-3,4-isopropylidene-D-mannitol and according to E, b 1,6-ditrityl-2,5-dimethyl-3,4-isopropylidene-D-mannitol, in yields of 85–90%.

Detritylation C or E, c

The acid-labile trityl group is removed in the presence of sulphuric acid and acetone. For this purpose, the particular ditrityl compound (D, E, b; 0.1 mol) is dissolved in 500 ml. acetone, mixed with 500 ml. methanol which contains 5 ml. concentrated sulphuric acid and warmed to 50° C. on a water-bath. After 60 minutes, the trityl radicals are split from the 1,6-position. One mixes with 1 l. diisopropylidene ether and extracts twice with 1 l. amounts of water, finally with 1 l. aqueous 1M $NaHCO_3$. The diisopropyl ether phase is evaporated and purified on silica gel. One obtains, according to D, c, 2,5-diallyl-3,4-isopropylidene-D-mannitol and, according to E, c, 2,5-dimethyl-3,4-isopropylidene-D-mannitol in yields of 90–95%.

Alkylation D or E, d

For the introduction of the substituents in 1,6-position, the compounds D, E-c, in each case 0.1 mol, are dissolved in 500 ml. toluene and mixed with potassium tert.-butylate (0.2 mol). One boils under reflux and adds dropwise, while stirring, in each case 0.2 mol of the corresponding compounds; for example, for the preparation of D, d, octadecyl mesylate bromide or iodide, for the preparation of E, d, octadec-(2')-enyl mesylate or bromide. After conclusion of the reaction (TLC verification), the toluene phase is extracted twice with water and evaporated. The residue from reaction D, d is mainly 1,6-dioctadecyl-2,5-diallyl-3,4-isopropylidene-D-mannitol, from E, d 1,6-dioctadec-(2')-enyl-2,5-dimethyl-3,4-isopropylidene-D-mannitol in yields of about 90%.

Deacetonisation D or E, e

For the removal of the isopropylidene group in the 3,4-position of the mannitol derivative, one uses aqueous sulphuric acid in 2-propanol/methanol 1:1. The particular intermediate product (0.1 mol) from D, E-d in 1 l. of the solvent mixture is mixed with 50 ml. 2N $H_2SO_4$ and boiled under reflux up to the complete splitting off of the isopropylidene group (TLC verification). One mixes with 1 l. diisopropyl ether, extracts twice with, in each case 1 l. of water and evaporates the diisopropylidene ether phase. The intermediate products are purified chromatographically on silica gel and characterised by microanalysis. One obtains D, I 1,6-dioctadecyl-2,5-diallyl-D-mannitol and E, I 1,6-dioctadec-(2')-enyl-2,5-dimethyl-D-mannitol in yields of about 90%.

The following compounds of the formula I were prepared in this way:

1,6-dioctadecyl-2,5-diallyl-D-mannitol ($C_{48}H_{96}O_6$; 769.30).
calc.: C 74.94, H, 12.58. found: C 74.51, H 12.31.

1,6-dioctadecyl-2,5-dipropargyl-D-mannitol ($C_{48}H_{94}O_6$; 719.24).
calc.: C 75.14, H 12.35. found: C 74.91, H 11.98.

1,6-dioctadec-(2')-enyl-2,5-dimethyl-D-mannitol ($C_{44}H_{88}O_6$; 713.19).
calc.: C 74.10; H 12.44. found: C 73.89, H 12.28.

1,6-dioctadec-(2')-enyl-2,5-dipropyl-D-mannitol $C_{48}H_{96}O_6$; 769.30).
calc.: C 74.94, H 12.58. found: C 74.61, H 12.31.

1,6-diallyl-2,5-dioctadecyl-D-mannitol ($C_{48}H_{96}O_6$; 769.30).
calc.: C 74.94, H 12.58. found: C 74.39, H 12.41.

1,6-dioctadec-(9')-enyl-2,5-dimethyl-D-mannitol ($C_{44}H_{88}O_6$; 713.19).
calc.: C 74.10, H 12.44. found: C 73.71, H 12.23.

1,6-dioctadecyl-2,5-dioctadec-(9')-enyl-D-mannitol ($C_{78}H_{154}O_6$; 1188.09).
calc.: C 78.85, H 13.07. found: C 78.49, H 12.86.

Diol splitting D, E-F

The intermediate products D, I and E, I (in each case 0.1 mol) are dissolved in 500 ml. benzene and mixed portionwise with lead tetraacetate (about 0.1 mol) until the starting product is no longer to be detected (TLC verification). The reaction mixture is washed twice with, in each case, 500 ml. water, the benzene phase is evaporated and the residue taken up in 500 ml. methanol.

Reduction D, E-g

The solution of the aldehydes in methanol is mixed portionwise with $NaBH_4$ (about 0.1 mol) until the aldehyde detection is negative. One mixes with 500 ml. diisopropyl ether and shakes out twice with water. The diethyl ether phase is evaporated and the residue chromatographed on silica gel. One obtains D, II, 1-octadecyl-2-allyl-sn-glycerol and E, II, 1-octadecyl-(2')-enyl-2-methyl-sn-glycerol in yields of about 95%.

Rearrangement D, E-h:

The reaction products D, II and E, II (0.1 mol) are dissolved in 20 ml. dimethylformamide and mixed with K tert.-butylate (0.15 mol). One heats so long at 100° to 110° C. (about 60 min.) that the displacement of the double bond is complete. One cools to 20° C., mixes with 200 ml. diisopropyl ether and extracts with 200 ml. water. The diethyl ether phase is evaporated and chromatographed on silica gel. One obtains D, II 1-octadecyl-2-propenyl-sn-glycerol in yields of about 90%.

The following compounds of the formula II are prepared in this way:

1-octadecyl-2-allyl-sn-glycerol ($C_{24}H_{48}O_3$; 384.65).
calc.: C 74.94, H, 12.58. found: C 74.69, H 12.44.

1-octadec-(9')-enyl-2-propyl-sn-glycerol ($C_{24}H_{48}O_3$; 384.65).
calc.: C 74.94, H 12.58. found: C 74.63, H 12.51.

1-octadec-(2')-enyl-2-methyl-sn-glycerol ($C_{22}H_{44}O_3$; 356.59).
calc.: C 74.10, H 12.44. found: C 73.89, H 12.37.

1-octadec-(1')-enyl-2-methyl-sn-glycerol ($C_{22}H_{44}O_3$; 356.59).
calc.: C 74.10, H 12.44. found: C 73.94, H 12.21.

1-octadec-(1')-enyl-2-dodecyl-sn-glycerol ($C_{33}H_{66}O_3$; 510.89).
calc.: C 77.58, H 13.02. found: C 77.06, H 12.82.

The free hydroxyl groups (sn-3-hydroxyl for A, D, E-II; sn-1-hydroxyl for B III and sn-2-hydroxyl for C, IV) present in the diethyl-glycerols are phosphorylated according to a general process and converted into a phosphoric acid dichloride, which represents the central intermediate product for the introduction of the radical $R_3$ (see in this regard reaction scheme F: phospholipids from diether-glycerols). Since the structural modification in this step of the synthesis only takes place in $R_3$, however in differing linkage with the phosphorus, for uniformity the different fundamental substances A II, B III and C IV are summarised under the symbol R'. The reaction scheme F describes, by way of example, some typical reactions which serve for the introduction of the radical $R_3$.

Phosphatidic acid chlorides V-VII

The intermediate compounds II–IV, for example from A-C (in each case 0.1 mol) are taken up in 500 ml. THF and mixed with 0.2 mol triethylamine. One adds the solution dropwise at 20° C., with stirring, to phosphorus oxychloride (0.15 mol) in 100 ml. THF. After ending of the reaction (TLC verification), the precipitated triethylamine hydrochloride is filtered off, mixed with 100 ml. toluene and evaporated on a rotary evaporator (removal of excess $POCl_3$). One obtains an oily residue which consists mainly of 1-octadecyl-2-methyl-sn-glycero-3-phosphodichloride (V), 3-octadecyl-2-methyl-sn-glycero-1-phosphodichloride (V) or 1-methyl-3-octadecyl-sn-glycero-3-phosphodichloride (VII) and is taken up in 400 ml. THF. The yield lies at 95%.

Phosphatidic acids VIII$_1$–X$_1$

The THF solutions of V–VII are, in each case, mixed at 10° C. with 80 ml. water and stirred so long that the hydrolysis is complete. One mixes with 300 ml. water and extracts with 300 ml. chloroform. The chloroform phase is mixed with 300 ml. methanol and shaken out with 300 ml. sodium hydrogen carbonate. After removal of the chloroform, the residue is chromatographed on silica gel. One obtains end products in yields of 90%, referred to the diether-glycerols, namely, 1-octadecyl-2-methyl-sn-glycero-3-phosphate (VIII$_1$), 3-octadecyl-2-methyl-sn-glycero-1-phosphate (IX$_1$) and 1-methyl-3-octadecyl-sn-glycero-2-phosphate (X$_1$).

The following compounds of the formula VIII$_1$–X$_1$ are prepared in this way:

1-octadecyl-2-methyl-sn-glycero-3-phosphate, sodium salt (C$_{22}$H$_{46}$O$_6$PNa; 460.58).
calc.: C 57.37, H 10.07, P 6.73. found: C 57.55, H 10.13, P 6.50.

3-octadecyl-2-methyl-sn-glycerol-1phosphate, sodium salt (C$_{22}$H$_{46}$O$_6$PNa; 460.55).
calc.: C 57.37, H 10.07, P 6.73. found: C 58.01, H 10.27, P 6.67.

1-methyl-3-octadecyl-sn-glycerol-2-phosphate, sodium salt (C$_{22}$H$_{46}$O$_6$PNa; 460.58).
calc.: C 57.37, H 10.07, P 6.73. found: C 57.46, H 10.10, P 6.51.

1-pentyl-3-octadecyl-sn-glycerol-2-phosphate, sodium salt (C$_{26}$H$_{54}$O$_6$PNa; 516.68).
calc.: C 60.44, H 10.54, P 4.45. found: C 60.50, H 10.77, P 4.23.

1-dodecyl-3-octadecyl-sn-glycerol-2-phosphate, sodium salt (C$_{33}$H$_{68}$O$_6$PNa; 614.87).
calc.: C 64.46, H 11.15, P 3.74. found: C 64.67, H 11.19, P 3.61.

Phosphatidylglycols VIII$_2$–X$_2$

The THF solutions of V–VII (0.1 mol in 400 ml. THF) are mixed dropwise at 20° C. with a solution of triethylamine (0.4 mol) in 100 ml. THF and then with ethylene glycol (0.2 mol) in 300 ml. THF. One warms to 40° C. After ending of the reaction (TLC verification), it is filtered off from triethylamine hydrochloride and mixed with 100 ml. water for the hydrolysis of the intermediate product. One adds a further 300 ml. of water thereto and extracts with chloroform. The residue from the chloroform phase is chromatographed on silica gel. One obtains VIII$_2$, 1-octadecyl-2-methyl-sn-glycero-3-phosphoglycol and the corresponding compounds IX$_2$ and X$_2$ in yields of about 90%.

Compounds of the formula VIII$_2$–X$_2$ 1-octadecyl-2-methyl-sn-glycero-3-phosphoglycol, sodium salt (C$_{24}$H$_{50}$NaO$_7$P; 504.63).
calc.: C 57.12, H 9.99, P 6.14. found: C 56.81, H 9.87, P 6.07.

3-octadecyl-2-methyl-sn-glycerol-2-phosphoglycol, sodium salt (C$_{24}$H$_{50}$NaO$_7$P; 504.63).
calc.: C 57.12, H 9.99, P 6.14. found: C 57.01, H 9.76, P 5.93.

1-octadec-(2')-enyl-2-methyl-sn-glycerol-2-phosphoglycol, sodium salt (C$_{24}$H$_{48}$NaO$_7$P; 502.61).
calc.: C 57.35, H 9.63, P 6.16. found: C 57.21, H 9.51, P 5.88.

Phosphatidylethanolamines VIII$_3$–X$_3$

The THF solutions of V–VII (0.1 mol in 400 ml. THF) are mixed dropwise at 20° C. with a solution of triethylamine (0.4 mol) in 100 ml. THF and then with ethanolamine (0.2 mol) in 300 ml. THF. One warms to 40° C. After ending of the reaction (TLC verification), it is filtered off from triethylamine hydrochloride, mixed with 100 ml. toluene and evaporated. The residue, the oxazaphospholane of II, III or IV, is taken up in 200 ml. 2-propanol and warmed to 60° C. with 150 ml. of 20% formic acid. After 60 min., the ring opening is complete. The phosphatidylethanolamines of the corresponding structure (VIII$_3$–X$_3$) precipitate out and, for complete purification, are also chromatographed on silica gel. The yields amount to about 90%, referred to the corresponding alcohols.

Compounds of the formula VIII$_3$–X$_3$ 1-octadecyl-2-methyl-sn-glycero-3-phosphoethanolamine (C$_{24}$H$_{52}$NO$_6$P; 481.66).
calc.: C 59.85, H 10.88, P 6.43. found: C 60.01, H 10.91, P 6.31.

3-octadecyl-2-methyl-sn-glycero-2-phosphoethanolamine (C$_{24}$H$_{52}$NO$_6$P; 481.66).
calc.: C 59.85, H 10.88, P 6.43. found: C 59.74, H 10.74, P 6.37.

Phosphatidic acid alkyl esters VIII$_4$–X$_4$

The THF solutions of V–VII (0.1 mol in 400 ml. THF) are mixed dropwise at 20° C. with a solution of triethylamine (0.4 mol) in 100 ml. THF and then with alcohol (0.2 mol) in 300 ml. THF. One warms to 40° C. After ending of the reaction, it is filtered off from triethylamine hydrochloride and mixed with 100 ml. H$_2$O for hydrolysis. One stirs up to the ending of the reaction (TLC verification), mixes with 400 ml. water and extracts with chloroform. The residue from the chloroform phase is further chromatographed on silica gel. One obtains the products VIII$_4$–X$_4$ in yields of about 90%.

Compounds of the formula VIII$_4$–X$_4$

1octadecyl-2-methyl-sn-glycero-3-phosphoric acid methyl ester, sodium salt (C$_{23}$H$_{48}$NaO$_6$P; 474.60).
calc.: C 58.21, H 10.20, P 6.53. found: C 58.16, H 10.04, P 6.41.

1-octadecyl-2-methyl-sn-glycero-3-phosphoric acid octyl ester, sodium salt ($C_{30}H_{62}NaO_6P$; 572.60).

calc.: C 62.91, H 10.91, P 5.41. found: C 62.56, H 10.82, P 5.42.

Phosphatidylcholines $VIII_5$–$X_5$:

The bromoalkyl-phosphatidic acids necessary for the preparation of phosphatidylcholines are obtained from bromoalkanols analogously to $VIII_4$–$X_4$. For the amination, the bromoalkyl esters of the corresponding phosphatidic acids (0.1 mol) are dissolved in 100 ml. chloroform and mixed with 100 ml. 2-propanol which contains 30 g. trimethylamine. After 8 hours at 50° C., it is shaken out against water, the chloroform phase is evaporated and the residue chromatographed on silica gel. The expected products result in about 90% yields.

Compounds of the formula $VIII_5$–$X_5$:

1-octadecyl-2-methyl-sn-glycerol-3-phosphocholine ($C_{27}H_{58}NO_6P$; 523.74).

calc.: C 61.92, H 11.16, P 5.91. found: C 61.95, H 11.18, P 5.76.

1-octadecyl-2-methyl-sn-glycero-3-phospho-N,N,N-trimethyl-hexanolamine ($C_{31}H_{66}NO_6P$; 579.85).

calc.: C 64.21, H 11.47, P 5.34. found: C 64.33, H 11.48, P 5.29.

1-octadecyl-2-pentyl-sn-glycerol-3-phosphocholine ($C_{31}H_{66}NO_6P$; 579.85).

calc.: C 64.21, H 11.47, P 5.34. found: C 64.49, H 11.55, P 5.17.

1-octadecyl-2-dodecyl-sn-glycerol-3-phosphocholine ($C_{38}H_{80}NO_6P$; 678.04).

calc.: C 67.31, H 11.89, P 4.57. found: C 67.46, H 11.94, P 4.41.

Phosphatidyl-N,N-dimethylethanolamines $VIII_6$–$X_6$:

One proceeds as described in $VIII_5$–$X_5$ but uses 30 g. dimethylamine in 100 ml. propanol in the amination step.

Compounds of the formula $VIII_6$–$X_6$:

1-octadecyl-2-methyl-sn-glycerol-3-phospho-N,N-dimethylethanolamine ($C_{26}H_{56}NO_6P$; 509.72).

calc.: C 61.27, H 11.07, P 6.08. found: C 61.35, H 11.14, P 5.96.

Phosphatidyl-N-methyl-ethanolamines $VIII_7$–$X_7$:

One proceeds as described in $VIII_5$–$X_5$ but uses 30 g. methylamine in 100 ml. 2-propanol in the amination step.

Compounds of the formula $VIII_7$–$X_7$:

1-octadecyl-2-methyl-sn-glycero-3-phospho-N-methylethanolamine ($C_{25}H_{54}NO_6P$; 495.69).

calc.: C 60.58, H 10.98, P 6.25. found: C 60.72, H 11.05, P 6.11.

Phosphatidylethanolamines $VIII_8$–$X_8$ (=$VIII_3$–$X_3$):

One proceeds as described under $VIII_5$–$X_5$ but uses 20 g. $NH_3$ in 100 ml. 2-propanol in the amination step.

Phosphatidylglycerols $VIII_9$–$X_9$:

The THF solutions of V–VII (0.1 mol in 400 ml. THF) are mixed dropwise at 20° C. with a solution of triethylamine (0.4 mol) in 100 ml. THF. Subsequent thereto, one adds dropwise 1,2-isopropylideneglycerol (0.2 mol) in 300 ml. THF. One warms to 40° C. After ending of the reaction (TLC verification), it is filtered off from precipitated triethylamine and the filtrate mixed at 10° C. with 100 ml. water and stirred until the hydrolysis is complete. After the addition of a further 100 ml. of water, the pH value of the aqueous phase is lowered with formic acid to pH 4–5 and stirred until the splitting off of the isopropylidene group is complete (TLC verification). One extracts with 300 ml. chloroform and treats the chloroform phase with 300 ml. 1M sodium hydrogen carbonate. The chloroform phase is evaporated and the residue chromatographed on silica gel. One obtains the desired products, $VIII_9$–$X_9$, in about 90% yield.

Compounds of the formula $VIII_9$–$X_9$:

3-octadecyl-2-methyl-sn-glycero-3-phosphoglycerol, sodium salt ($C_{25}H_{52}NaO_8P$; 534.66).

calc.: C 56.16, H 9.80, P 5.79. found: C 56.09, H 9.51, P 5.99.

3-octadecyl-2-pentyl-sn-glycero-3-phosphoglycerol, sodium salt ($C_{29}H_{60}NaO_8P$; 590.77).

calc.: C 58.96, H 10.24, P 5.24. found: C 58.51, H 10.03, P 5.01.

3-octadecyl-2-dodecyl-sn-glycero-3-phosphoglycerol, sodium salt ($C_{36}H_{74}NaO_8P$; 688.95).

calc.: C 62.76, H 10.83, P 4.72. found: C 63.04, H 10.94, P 4.53.

Phosphatidylserines $VIII_{10}$–$X_{10}$:

The THF solutions of V–VII are, as described in $VIII_1$–$X_1$, converted into phosphatidic acids (0.1 mol). The sodium salt of the purified phosphatidic acids (0.1 mol) is dissolved in 200 ml. $CHCl_3$, mixed with 200 ml. methanol and washed out with 200 ml. 1N HCl. The chloroform phase is evaporated and dried in a vacuum. The free phosphatidic acid (0.1 mol) is mixed with commercially-available N-carbobenzoxy-L-serine benzyl ester (0.2 mol) and 500 ml. pyridine added thereto. To this one adds a solution of commercial triisopropylbenzene-sulphonic acid chloride (0.3 mol) in 500 ml. pyridine and warms to 70° C. until the solution is clear. After 3 hours stirring at 20° C., one mixes with 600 ml. chloroform and stirs for a further 60 minutes. The reaction mixture is then washed with 500 ml. of water and the chloroform phase evaporated. One chromatographs on silica gel; one obtains the protected phosphatidylseries in about 50% yield.

The protected intermediate product (0.05 mol) are dissolved in 1 l. glacial acetic acid and mixed with 4 g. Pd/C (10%) and 0.4 g. palladium black. One stirs so long in $H_2$ atmosphere until the hydrogen take-up ceases. The protected phosphatidylserines are converted quantitatively into the free phosphatidylserines VIII$_{10}$–X$_{10}$. The acetic acid solution is warmed, filtered and mixed with 1 l. acetone. One obtains a chromatographically uniform substance as fine, amorphous powder.

Compounds of the formulae VIII$_{10}$–X$_{10}$:

1-octadecyl-2-methyl-sn-glycero-3-phosphoserine, sodium salt (C$_{25}$H$_{51}$NNaO$_8$P; 547.66).

calc.: C 54.83, H 9.39, N 2.56, P 5.66. found: C 54.71, H 9.31, N 2.49, P 5.39.

3-octadecyl-2-methyl-sn-glycero-3-phosphoserine, sodium salt (C$_{25}$H$_{51}$NNaO$_8$P; 547.66).

calc.: C 54.83, H 9.39, N 2.56, P 5.66. found: C 54.59, H 9.24, N 2.41, P 5.43.

Phosphatidylamides VIII$_{11}$–X$_{11}$

The THF solutions of V–VII (0.1 mol in 400 ml. THF) are mixed dropwise at 20° C., while stirring, with a solution of triethylamine (0.2 mol) in 100 ml. THF. Subsequently thereto, one adds drop-wise bis-(chloroethyl)-amine (0.15 mol) in 300 ml. THF. After ending of the reaction (TLC verification), it is filtered off from precipitated triethylamine hydrochloride and the filtrate hydrolysed by the addition of 100 ml. of water. After ending of the hydrolysis, it is extracted with 400 ml. chloroform and the chloroform phase further washed with 400 ml. of a 0.5M sodium hydrogen carbonate solution. The residue is chromatographed on silica gel. One obtains the desired products, VIII$_{11}$–X$_{11}$, in about 80% yield.

Compounds of the formulae VIII$_{11}$–X$_{11}$:

1-octadecyl-2-methyl-sn-glycero-3-phospho-bis(chloroethyl)-amide (C$_{26}$H$_{53}$Cl$_2$NNaO$_5$P; 584.60).

calc.: C 53.42, H 9.14, N 2.40, P 5.30. found: C 53.21, H 9.08, N 2.26, P 6.16.

SUMMARY

The invention concerns D-mannitol derivatives of the general formula I

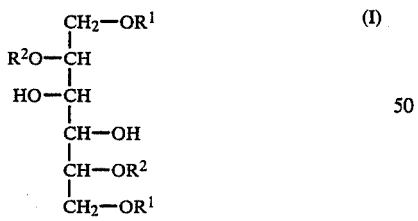

(I)

wherein R$^1$ and R$^2$ are the same or different, and when R$^1$ and R$^2$ are the same, signify a straight-chained or branched alkyl, alkenyl or alkynyl group with 6 to 24 carbon atoms, which can contain cycloalkyl radicals with 3 to 6 carbon atoms, aryl radicals, benzyloxy, allyloxy, mesyloxy and/or halogen substituents and, when R$^1$ and R$^2$ are different, signify a straight-chained or branched alkyl group with 1 to 24 carbon atoms, which can contain cycloalkyl radicals with 3 to 6 carbon atoms, aryl radicals, benzyloxy, allyloxy, mesyloxy and/or halogen substituents, or a straight-chained or branched alkenyl or alkynyl group with 3 to 24 carbon atoms, which can contain cycloalkyl radicals with 3 to 6 carbon atoms, aryl radicals, benzyloxy, allyloxy, mesyloxy and/or halogen substituents, and R$^1$ can also be trityl. Starting from these D-mannitol derivatives, there can be obtained, in simple manner and with good yields, phospholipids in the form of their optically pure stereoisomers.

I claim:

1. Glycerol derivatives of the general formula II, III or IV

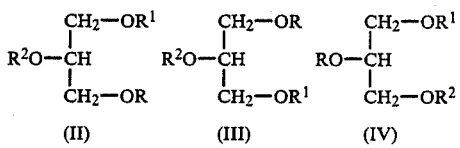

wherein when R$^1$ and R$^2$ are the same, they signify a substituted or unsubstituted straight-chained or branched alkyl, alkenyl or alkynyl group with 6 to 24 carbon atoms, the substituents being cycloalkyl radicals with 3 to 6 carbon atoms, aryl radicals, benzyloxy, allyloxy, mesyloxy and/or halogen substituents, and when R$^1$ and R$^2$ are different, R$^1$ signifies a substituted or unsubstituted straight-chained or branched alkyl group with 1 to 9 carbon atoms, and R$^2$ signifies a substituted or unsubstituted straight-chained or branched alkenyl group with 10–24 carbon atoms and with 1 or more double bonds, the substituents in each case being cycloalkyl radicals with 3 to 6 carbon atoms, aryl radicals, benzyloxy, allyloxy, mesyloxy and/or halogen substituents, or substituted or unsubstituted cycloalkyl radicals with 3 to 6 carbon atoms, aryl radicals, benzyloxy, allyloxy, mesyloxy and/or halogen substituents, and R$^1$ can also be trityl; and R is a hydrogen atom or the radical

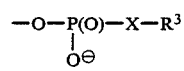

wherein X=O, NH or NR$^3$ and, when X=O, R$^3$ signifies H, alkyl, alkenyl or alkynyl with 1 to 18 carbon atoms, haloalkyl with 2 to 14 carbon atoms, 2-amino-2-carboxyethyl, dihydroxypropyl, pentahydroxyhexyl, amino alkyl with 2 to 14 carbon atoms, N-methylaminoalkyl with 2 to 14 carbon atoms, N,N-dimethylaminoalkyl with 2 to 14 carbon atoms, N,N,N-trimethylaminoalkyl with 2 to 14 carbon atoms, N-[N',N',N'-trimethyl)-aminoethyl]-N,N-dimethylaminoethyl, when X=NH, R$^3$ signifies H, alkyl or alkenyl with 1 to 10 carbon atoms, haloalkyl with 2 to 6 carbon atoms, hydroxyethyl, dihydroxypropyl, aminoalkyl, and when X=NR$^3$, R$^3$ signifies alkyl, alkenyl with 1 to 10 carbon atoms, bis-chloroethyl, and whereby, when R is not a hydrogen atom, one of the radicals R$^1$ or R$^2$ in formulae II, III or IV can also be a hydrogen atom.

2. Glycerol derivatives of the general formula II, III or IV

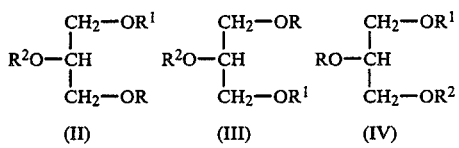

wherein $R^1$ and $R^2$ are the same or different and, when $R^1$ and $R^2$ are the same, signify a substituted or unsubstituted straight-chained or branched alkyl, alkenyl or alkynyl group with 6 to 24 carbon atoms, the substituents being cycloalkyl radicals with 3 to 6 carbon atoms, aryl radicals, benzyloxy, allyloxy, mesyloxy and/or halogen substituents, and when $R^1$ and $R^2$ are different signify a substituted or unsubstituted straight-chain or branched alkyl group with 1 to 24 carbon atoms, the substituents being cycloalkyl radicals with 3 to 6 carbon atoms, aryl radicals, benzyloxy, allyloxy, mesyloxy and/or halogen substituents, or substituted or unsubstituted cycloalkyl radicals with 3 to 6 carbon atoms, aryl radicals, benzyloxy, allyloxy, mesyloxy and/or halogen substituents, and $R^1$ can also be trityl and R represents a hydrogen atom or the radical

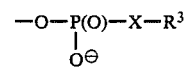

wherein X is NH or $NR^3$ and, when X=NH, $R^3$ signifies H, alkyl or alkenyl with 1 to 10 carbon atoms, haloalkyl with 2 to 6 carbon atoms, hydroxyethyl, dihydroxypropyl, aminoalkyl, and when X=$NR^3$, $R^3$ signifies alkyl, alkenyl with 1 to 10 carbon atoms, bis-chloroethyl, and whereby, when R is not a hydrogen atom, one of the radicals $R^1$ or $R^2$ in formulae II, III or IV can also be a hydrogen atom.

3. Glycerol derivatives of the formula

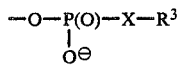

wherein $R^1$ and $R^2$ are the same or different and, when $R^1$ and $R^2$ are the same, signify a substituted or unsubstituted straight-chain or branched alkyl, alkenyl or alkynyl group with 6 to 24 carbon atons, the substituents being cycloalkyl radicals with 3 to 6 carbon atoms, aryl radicals, benzyloxy, allyloxy, mesyloxy and/or halogen substituents, and when $R^1$ and $R^2$ are different signify a substituted or unsubstituted straight-chain or branched alkyl group with 1 to 24 carbon atoms, the substituents being cycloalkyl radicals with 3 to 6 carbon atoms, aryl radicals, benzyloxy, allyloxy, mesyloxy and/or halogen substituents, or substituted or unsubstituted cycloalkyl radicals with 3 to 6 carbon atoms, aryl radicals, benzyloxy, allyloxy, mesyloxy and/or halogen substituents, and $R^1$ can also be trityl and R represents a hydrogen atom or the radical

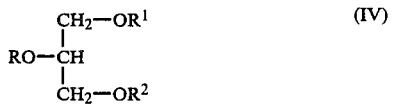

wherein X=O, NH or $NR^3$ and, when X=O, $R^3$ signifies H, alkyl, alkenyl or alkynyl with 1 to 18 carbon atoms, haloalkyl with 2 to 14 carbon atoms, 2-amino-2-carboxyethyl, dihydroxypropyl, pentahydroxyhexyl, amino alkyl with 2 to 14 carbon atoms, N-methylaminoalkyl with 2 to 14 carbon atoms, N,N-dimethylaminoalkyl with 2 to 14 carbon atoms, N,N,N-trimethylaminoalkyl with 2 to 14 carbon atoms, N-[N',N',N'-trimethyl)-aminoethyl]-N,N-dimethylaminoethyl, when X=NH, $R^3$ signifies H, alkyl or alkenyl with 1 to 10 carbon atoms, haloalkyl with 2 to 6 carbon atoms, hydroxyethyl, dihydroxypropyl, aminoalkyl, and when X=$NR^3$, $R^3$ signifies alkyl, alkenyl with 1 to 10 carbon atoms, bis-chloroethyl, and whereby, when R is not a hydrogen atom, one of the radicals $R^1$ or $R^2$ can be a hydrogen atom.

4. Medicaments, containing an anti-tumor effective amount one or more of the compounds according to claims 1, 2 or 3, in which R signifies the radical

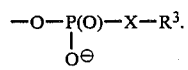

* * * * *

UNITED STATES PATENT AND TRADEMARK OFFICE
CERTIFICATE OF CORRECTION

PATENT NO. : 4,734,225

DATED : March 29, 1988

INVENTOR(S) : Hansjörg Eibl

It is certified that error appears in the above-identified patent and that said Letters Patent is hereby corrected as shown below:

Col. 5, line 48; "the object" should read --the subject--.

Col. 13, about line 50, on left side of formula entry #1, "$CH_2-O-(CH_2)_{17}-$" should read --$CH_2-O-(CH_2)_{17}-CH_3$--.

Col. 17. about line 30, on left side of formula entry #5, "R'--PO--O" should read --R'O--PO--O--.

Col. 24, line 66, "phosphodichloride (V)" should read --phosphodichloride (VI)--.

Col. 26, line 62, "1octadecyl" should read --1-octadecyl--.

Col. 28, lines 62-63, "phosphatidylseries" should read --phosphatidylserines--.

Signed and Sealed this

Tenth Day of January, 1989

*Attest:*

DONALD J. QUIGG

*Attesting Officer*      *Commissioner of Patents and Trademarks*